US012773319B2

(12) United States Patent
Daudet

(10) Patent No.: US 12,773,319 B2
(45) Date of Patent: Oct. 27, 2026

(54) CERAMIC JOINT IMPLANT PROVIDED WITH LOCKING DEVICE FOR SCREWING IT

(71) Applicant: FX SOLUTIONS, En-Bresse (FR)

(72) Inventor: Jean-Marie Daudet, En-Bresse (FR)

(73) Assignee: FX Shoulder Solutions, Viriat (FR)

( * ) Notice: Subject to any disclaimer, the term of this patent is extended or adjusted under 35 U.S.C. 154(b) by 414 days.

(21) Appl. No.: 18/493,871

(22) Filed: Oct. 25, 2023

(65) Prior Publication Data

US 2024/0138990 A1 May 2, 2024

(30) Foreign Application Priority Data

Oct. 27, 2022 (FR) .................................. FR2211231

(51) Int. Cl.

| | |
|---|---|
| ***A61B 8/00*** | (2006.01) |
| ***A61F 2/30*** | (2006.01) |
| *A61F 2/40* | (2006.01) |

(52) U.S. Cl.

CPC ..................... *A61F 2/30749* (2013.01); *A61F 2002/30069* (2013.01); *A61F 2002/30405* (2013.01); *A61F 2002/30495* (2013.01); *A61F 2002/3085* (2013.01); *A61F 2002/4085* (2013.01); *A61F 2310/00179* (2013.01)

(58) Field of Classification Search

CPC .. A61F 2002/30069; A61F 2002/30405; A61F 2002/3085; A61F 2002/30495; A61F 2002/40; A61F 2002/85

See application file for complete search history.

(56) References Cited

U.S. PATENT DOCUMENTS

| | | | | |
|---|---|---|---|---|
| 2013/0150975 A1* | 6/2013 | Iannotti | ................. | A61F 2/4059 623/19.11 |
| 2018/0161169 A1* | 6/2018 | Cardon | ................. | A61F 2/4081 |
| 2019/0298537 A1* | 10/2019 | Gargac | .................. | A61F 2/4081 |

FOREIGN PATENT DOCUMENTS

| | | |
|---|---|---|
| EP | 0884032 | 12/1998 |
| EP | 2689750 | 1/2014 |
| FR | 2802799 | 6/2001 |

* cited by examiner

*Primary Examiner* — Joel F Brutus

(74) *Attorney, Agent, or Firm* — Defillo & Associates, Inc.; Evelyn A. Defillo

(57) ABSTRACT

A joint prosthesis implant having: a main body made mainly of ceramic and including a joint outer surface made of ceramic, of concave or convex shape, at least one tightening screw configured to tighten the main body on the patient's bone or on an intermediate element attached to the bone, at least one added ring in the main body configured to homogeneously distribute in the main body the mechanical stresses caused by tightening the tightening screw, the added ring having a first member and a second member separate from each other.

10 Claims, 5 Drawing Sheets

CERAMIC JOINT IMPLANT PROVIDED WITH LOCKING DEVICE FOR SCREWING IT

FIELD OF THE INVENTION

The invention relates to a joint prosthesis implant. More specifically, the invention relates to a joint prosthesis implant whose joint outer surface is made of ceramic.

BACKGROUND OF THE INVENTION

The state of the art already describes several types of joint prosthesis, for example shoulder prostheses, hip prostheses and knee prostheses.

These joint prostheses all comprise two implants, each having a joint outer surface intended to come into contact with each other, thus reproducing the joint. To reproduce the best possible joint quality, it is known to use pairs of favorable materials for these joint outer surfaces in contact, these pairs possibly consisting of two "hard" materials or one "hard" material and one "soft" material. The "hard" materials known and used in joint prosthesis implants are the cobalt-chromium alloy, titanium-stainless steel alloy and ceramic. The "soft" materials may be plastic, for example ultra-high-molecular-weight polyethylene (UHMWPE) or polyetheretherketone (PEEK) or polyetherketoneketone (PEKK) and their derivatives.

The cobalt-chromium alloy is particularly appreciated by joint prosthesis implant manufacturers since it offers exceptional tribological and mechanical properties which allowed in particular the implant concerned to be screwed and tightened (using one or more screws located in the implant) either directly into the patient's bone, or into an element itself attached to the patient's bone (for example a metagene for a reverse total shoulder prosthesis), with no risk of damaging the implant.

However, the latest applicable standards (and in particular the updated standard of the delegated regulation (UE) 2020/217 of 4 Oct. 2019 REACH) tend to prohibit the use of chromium cobalt as material for the joint prosthesis implants since cobalt is considered to be a potentially carcinogenic, mutagenic or toxic substance for the patient. Alternative hard materials must therefore be considered.

One known hard material is ceramic. This material offers the advantage of being biocompatible and especially suitable for rubbing due to its hardness properties. However, ceramic is a material with very low ductility and the very high, localized mechanical stresses caused by the above-mentioned tightening using one or more screws could create cracks in the ceramic, or even break it. Such a risk is not acceptable, whether for the surgeon during the operation or for the patient who could need to have the prosthesis replaced too quickly. In addition, it is not currently authorized to install another ceramic implant when the ceramic of a first implant has broken. In this case therefore, another pair of materials must be chosen.

OBJECT AND SUMMARY OF THE INVENTION

To overcome these disadvantages, the state of the art already describes joint prosthesis implants comprising an element added by clipping between a glenosphere, whose joint outer surface is made of ceramic, and a tightening screw intended to be introduced by tightening into the patient's bone (or into an intermediate metagene when the patient's bone is a glenoid). This added element is used to distribute the mechanical stresses caused by tightening the tightening screw, homogeneously in the ceramic glenosphere, so that it does not crack or break. However, such solutions are not satisfactory since they do not guarantee the resistance of said added element, whether when tightening the tightening screw or over time, after the operation. It has been observed in fact that this added element, under the action of the local stresses applied by the screw head when the screw is being tightened, deforms considerably thereby causing it to become unclipped from the glenosphere. Consequently, these solutions do not guarantee a homogeneous distribution of the mechanical stresses resulting from the tightening in the ceramic glenosphere which could crack or break during the operation or very shortly afterwards. In addition, after the operation and during the lifetime of the prosthesis, this added element also undergoes local stresses which may generate a similar inconvenience, resulting in identical consequences for the integrity of the ceramic glenosphere.

The invention aims in particular to allow the use of such a ceramic implant provided with an added element which overcomes all the above-mentioned disadvantages.

This Invention Therefore Relates to an Implant Comprising:

- a main body made mainly of ceramic and comprising a joint outer surface made of ceramic, of concave or convex shape,
- at least one tightening screw configured to tighten the main body on the patient's bone or on an intermediate element attached to said bone,
- at least one added ring in the main body and forming with it a chamber trapping the head of the tightening screw and comprising a bearing surface forming a stop for said head of the tightening screw, the added ring being configured to be in contact with the tightening screw during said tightening, the added ring (4) comprising a central hole crossed by the tightening screw, the added ring being configured to homogeneously distribute in the main body the mechanical stresses caused by tightening the tightening screw, the added ring comprising a first member forming the outer surface of the added ring and comprising means for clipping to the main body and a second member acting as a spacer between the first member and the tightening screw, said second member being assembled in the first member, forming said bearing surface and defining the central hole, the first member and the second member being two members separate from each other and comprising locking means configured to prevent them from separating from each other after assembly.

Thus, a joint prosthesis implant made of ceramic (or mainly of ceramic) that is both functional and robust and that is not likely to crack or break when tightening the tightening screw (or after the operation) can therefore be produced. The joint prosthesis implant according to the invention reduces in fact the mechanical stresses transmitted to the main body, caused by tightening the tightening screw, compared with the solutions of the prior art, thanks in particular to the assembly between the first member and the second member of the added ring. Since the stresses eventually transmitted to the main body of the glenosphere, by the first member of the added ring, are homogeneously distributed in the main body, the risks of the main ceramic body cracking or breaking are reduced drastically, whether when tightening the tightening screw or after the operation. "Homogeneous distribution of the mechanical stresses caused by tightening the screw" means that the stresses are distributed over the entire surface of the main body in contact with the added ring (more precisely with its first member), thereby preventing a stress, which would be greater than the elastic limit and which would break the ceramic, from being applied on the main ceramic body. Due to the large radial contact area between the first member of the added ring and the main body, the forces can be distributed over a larger area of the main body so that the localized stresses are as low as possible.

In addition, the second member prevents any deformation of the first member when tightening the tightening screw into the patient's bone or into the intermediate element attached to said bone. Thus, this prevents the means for clipping the first member of the added ring to the main body of the glenosphere from becoming unclipped, making the use of the implant even safer.

In addition, the means for locking the assembly between the first member and the second member prevent them from separating after assembly, both when tightening the tightening screw into the patient's bone or into the intermediate element attached to said bone and before the operation (for example due to vibrations transmitted to the added ring when transporting the implant), or after the operation (for example due to vibrations resulting from the patient's activities). Thus, this optimizes the robustness and resistance over time of the implant.

The added ring (and therefore the first member and/or the second member) can be made of any material allowing the mechanical stresses to be evenly distributed in the main body. The first member and/or the second member can in particular be made entirely or partially of metal, plastic or ceramic. It can also be made of several different materials, including a composition of the above-mentioned materials.

According to other optional characteristics of the joint prosthesis implant according to the invention taken alone or in combination:

- the first member comprises a tapped portion and the second member comprises a corresponding threaded portion, the threaded portion and the tapped portion being configured so that the second member can be screwed to the first member, preferably, the direction of screwing of the second member to the first member being the opposite of that carried out when tightening the tightening screw,
- the tapped portion and the threaded portion have a left-hand pitch or a right-hand pitch, preferably of between 0.5 mm and 2 mm, the threaded portion preferably being a metric thread, a buttress thread or a square thread,
- the locking means comprise a circular channel and a collar configured to engage in said channel, the channel being formed on the first member or on the second member and the collar being respectively formed on the second member or the first member,
- the locking means comprise at least one clip and at least one hole configured to be crossed by the clip, the clip being formed on the first member or on the second member and the hole being respectively formed on the second member or the first member,
- the first member comprises elastically deformable peripheral means,
- the main body is a glenosphere, the tightening screw being configured to tighten the glenosphere onto a metagene attached to the patient's glenoid,
- the diameter of the glenosphere is between 30 and 46 mm, and/or
- the main body is a ceramic tibial plateau, a knee condyle, an anatomic glenoid, a hip acetabulum or a ceramic cup.

The invention also relates to a joint prosthesis comprising an implant according to any one of the preceding variants.

BRIEF DESCRIPTION OF THE FIGURES

The invention will be better understood on reading the following description, given solely by way of example and with reference to the accompanying drawings in which.

DETAILED DESCRIPTION

Figure 1:
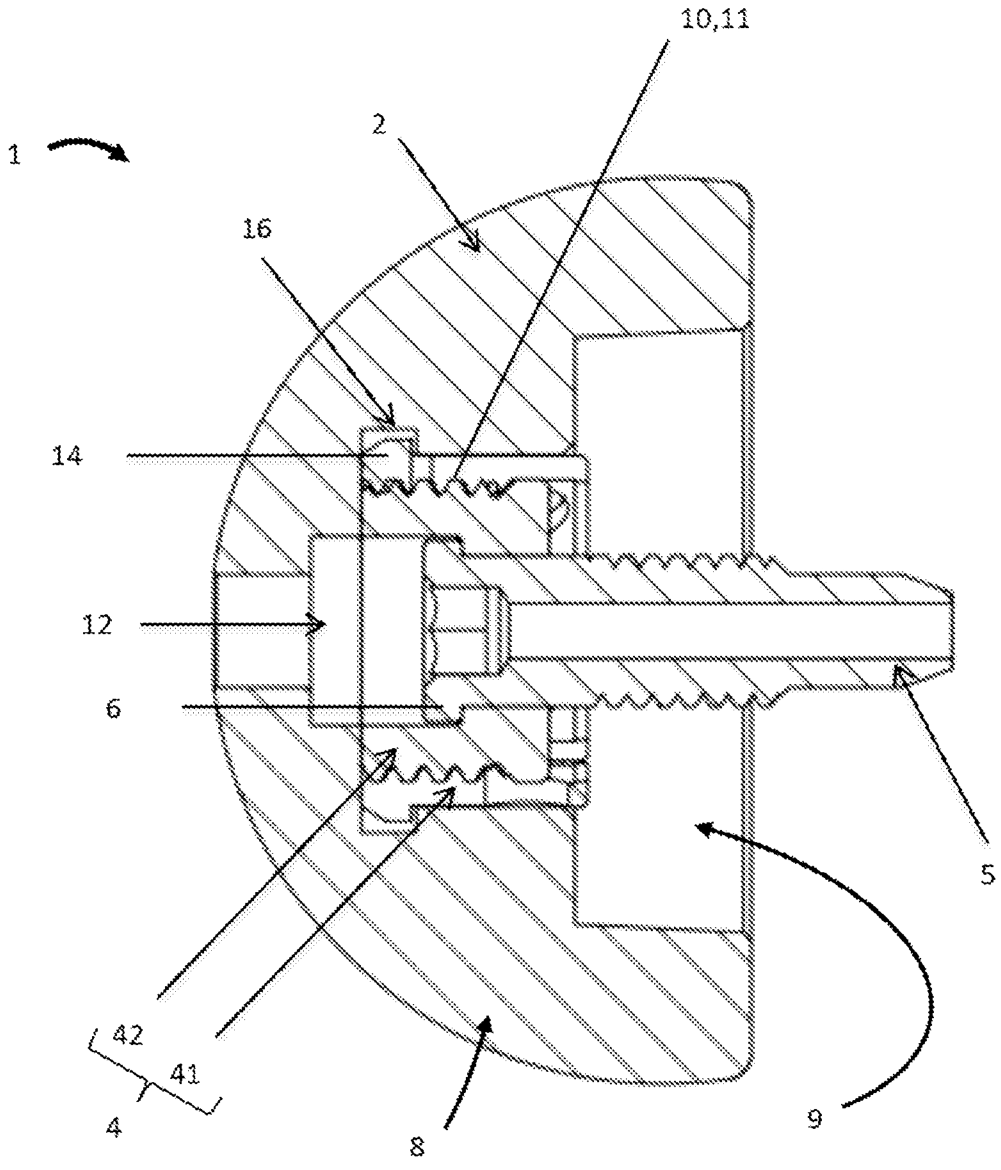
FIG. 1 is a cross-sectional view of a joint prosthesis implant according to the invention.
Figure 2:
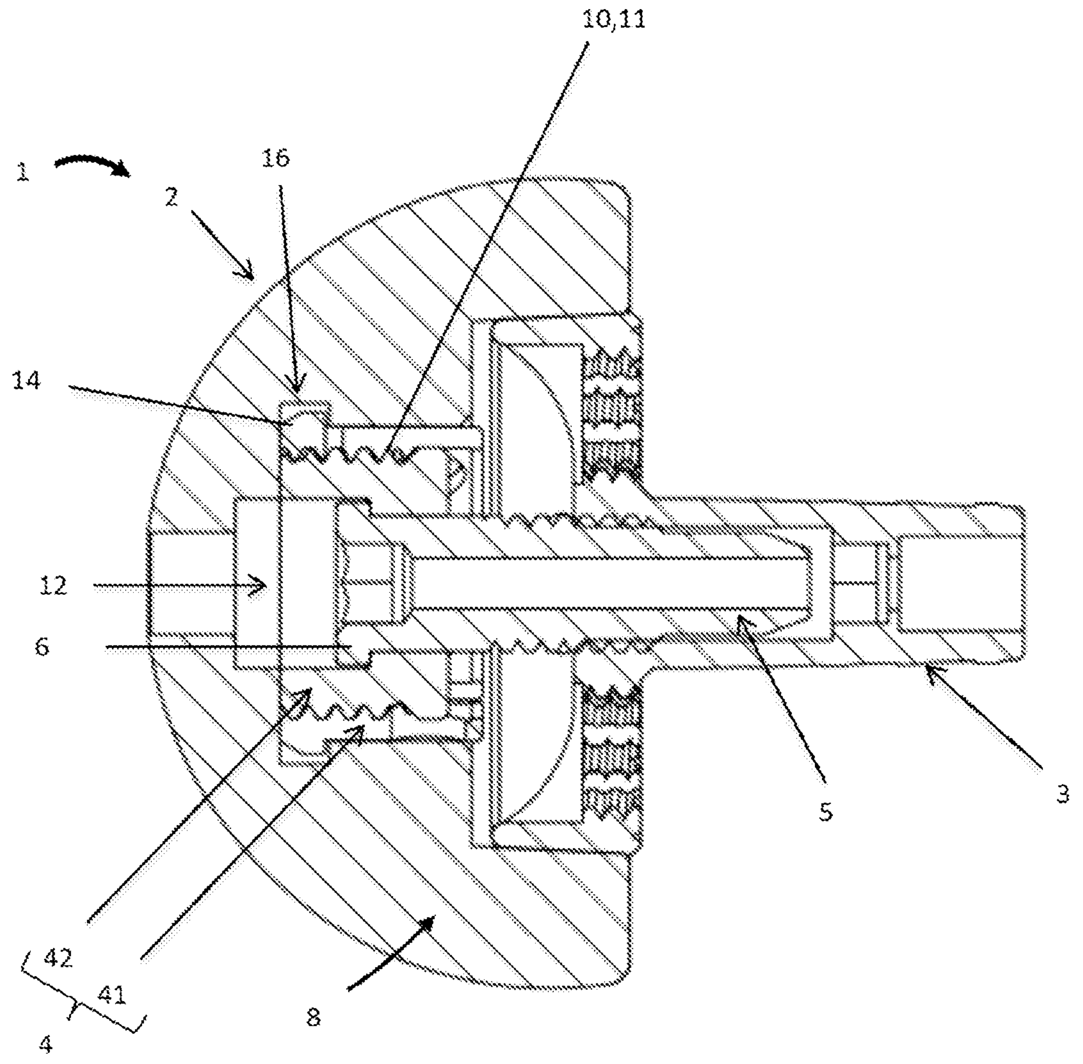
FIG. 2 is a cross-sectional view of the implant of FIG. 1 assembled to a metagene.
Figure 3A:
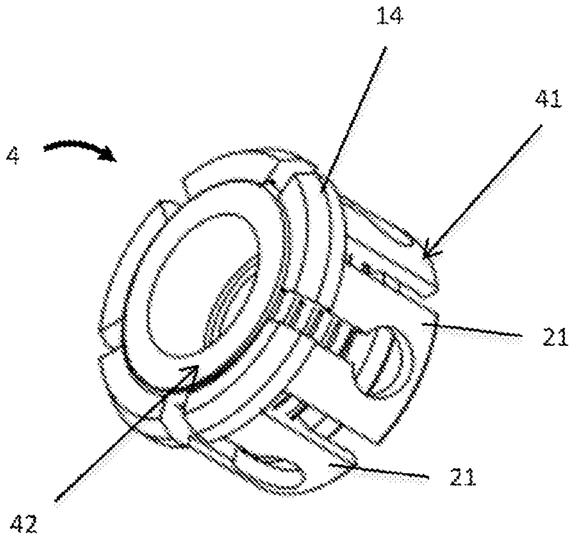
FIG. 3 is a perspective view (FIG. 3A), plan view (FIG. 3B) and cross-sectional view (3C) of an added ring as present in the implant of FIGS. 1 and 2.
Figure 3B:
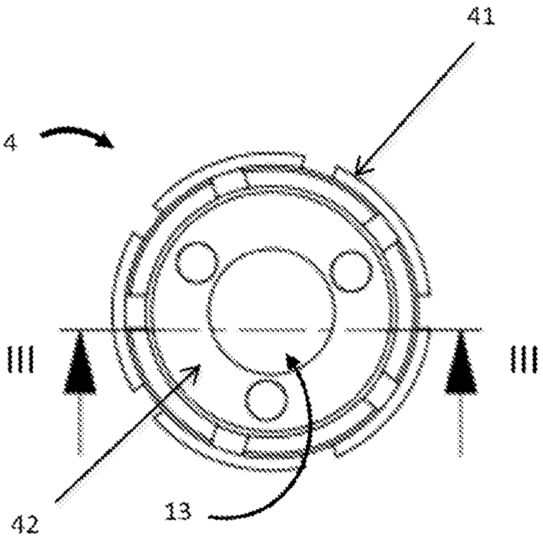
Figure 3C:
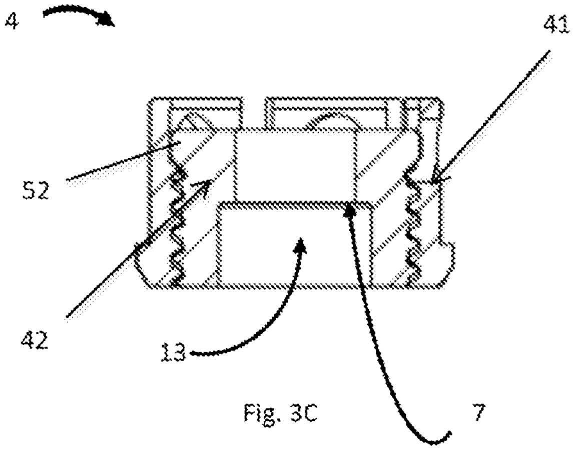

FIGS. 1 and 2 show a joint prosthesis implant according to a first embodiment of the invention, designated by the general reference 1. FIGS. 3A to 5C show an added ring, designated by the general reference 4 or one of its two constituent members. Note that the similar elements shown on the figures are designated by the same references.

The Joint Prosthesis Implant 1 Thus Described Comprises:

- a main body 2 made mainly of ceramic and comprising a joint outer surface 8 made of ceramic, of concave or convex shape,
- at least one tightening screw 5 configured to tighten the main body 2 on the patient's bone or on an intermediate element 3 attached to said bone,
- at least one added ring 4 in the main body 2 and forming with it a chamber 12 trapping the head 6 of the tightening screw 5 and comprising a bearing surface 7 forming a stop for said head 6 of the tightening screw 5, the added ring 4 being configured to be in contact with the tightening screw 5 during said tightening, the added ring 4 comprising a central hole 13 crossed by the tightening screw 5, the added ring 4 being configured to homogeneously distribute in the main body 2 the mechanical stresses caused by tightening the tightening screw 5. The added ring 4 comprises a first member 41 forming the outer surface of the added ring 4 and comprising means 14 for clipping to the main body 2 and a second member 42 acting as a spacer between the first member 41 and the tightening screw 5, said second member 42 being assembled in the first member 41, forming said bearing surface 7 and defining the central hole 13, the first member 41 and the second member 42 being two members separate from each other and comprising locking means 51, 52 configured to prevent them from separating from each other after assembly.

In the embodiment described with reference to the figures, the main body 2 corresponds to a glenosphere 2 which has a tightening screw 5 used to tighten it to an intermediate element 3 attached to the bone, in this case the metaglene 3.

The ceramic glenosphere 2 can have a diameter from 30 to 46 mm, it can be centered or off-centered and can be lateralized if necessary.

The glenosphere 2 and the metaglene 3 are assembled together using the tightening screw 5. To make the assembly even better, a Morse cone (not shown) is provided between the glenosphere 2 and the metaglene 3.

The glenosphere 2 comprises a housing 9 dimensioned to receive the added ring 4 and forming with it the chamber 12 trapping the head 6 of the tightening screw 5.

The joint prosthesis implant described therefore corresponds to a glenoid implant for reverse shoulder prosthesis. Nevertheless, the characteristics described within the framework of this embodiment can be applied to any prosthesis comprising a joint implant having a ceramic joint surface and being screwed and tightened using at least one tightening screw, on the patient's bone or on an intermediate element attached to said bone. For example, the invention also relates to implants for hip or knee prostheses.

Any type of ceramic known by those skilled in the art can be used for the main body. For example, it could be alumina, zirconia or a composite material. Since ceramic is a hard material, it can be used with pairs of "hard/hard" or "hard/soft" materials. In this second example, the "soft" material can be ultra-high-molecular-weight polyethylene (UHMWPE) or polyetheretherketone (PEEK) or polyetherketoneketone (PEKK) or their derivatives.

As specified previously, the added ring 4 is clipped into the housing 9 of the glenosphere 2 using clipping means, present partially on its first member 41, and thus forming, with the housing 9, the chamber 12 trapping the head 6 of the tightening screw 5. More precisely, the clipping means consist of teeth present at the ends of elastically deformable peripheral means (consisting of fins 21), forming together a rib 14, and of a circular groove 16 formed in the housing 9 of the glenosphere 2 and having a shape adapted to receive and lock the rib 14 formed by the teeth, so that the first member 41 can be clipped to the added ring 4. More precisely, the elasticity conferred to the first member 41 by its elastically deformable fins 21 allows it to deform sufficiently to insert the rib 14 in the groove 16. When the fins 21 return to their initial shape, the rib 14 is jammed in the groove 16, thereby clipping the first member 41 in the housing 9 of the glenosphere 2. Thus, there is a large contact area between the first member 41 and the glenosphere 2, in other words the entire radial contact area between the rib 14 and the groove 16. It is therefore possible to homogeneously distribute over this large contact area between the housing 9 of the glenosphere 2 and the added ring 4 the force of the stresses undergone locally by the ceramic glenosphere 2 and therefore, finally, to minimize this force, which reduces the risk of cracking or breaking the glenosphere.

Figure 4A:
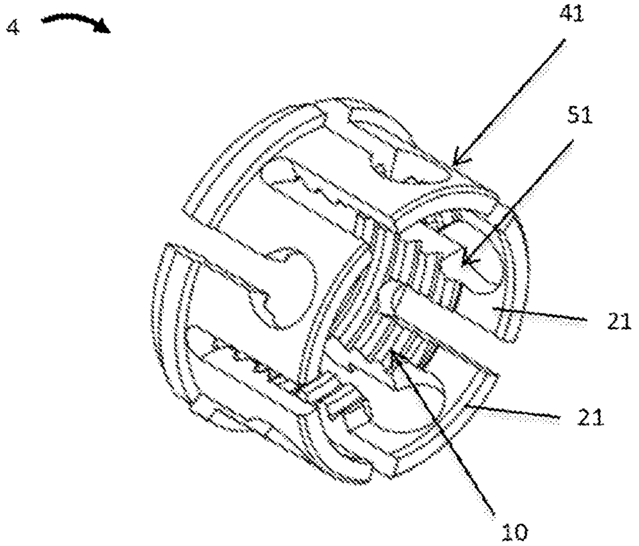
FIG. 4 is a perspective view (FIG. 4A), plan view (FIG. 4B) and cross-sectional view (4C) of a first member of the added ring of FIG. 4.
Figure 4B:
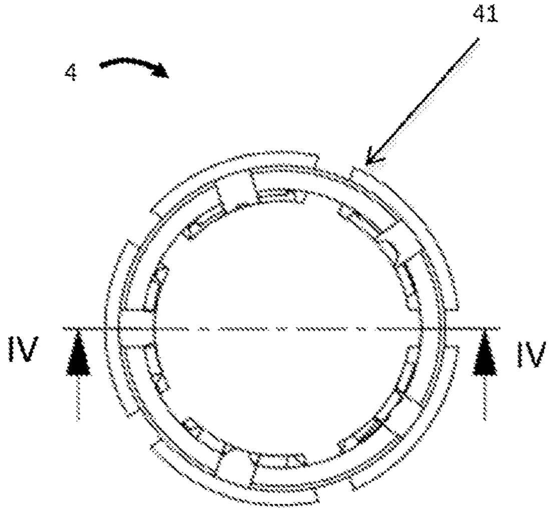
Figure 4C:
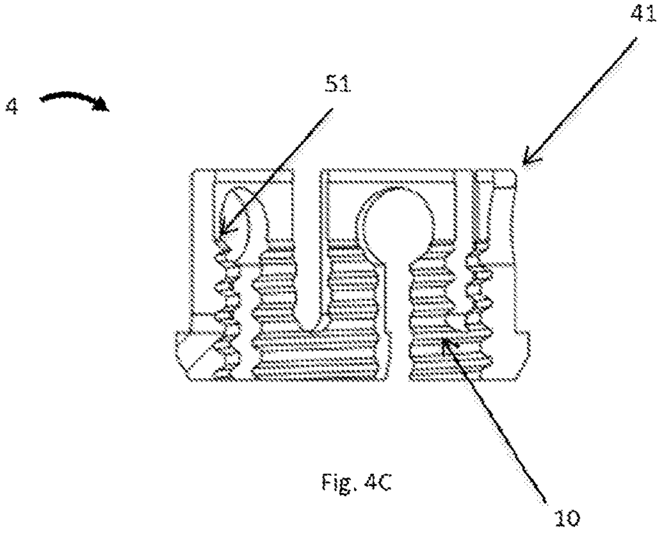
Figure 5A:
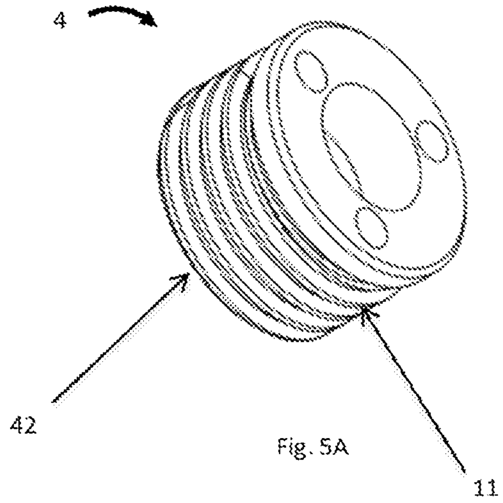
FIG. 5 is a perspective view (FIG. 5A), plan view (FIG. 5B) and cross-sectional view (5C) of a second member of the added ring of FIG. 4.
Figure 5B:
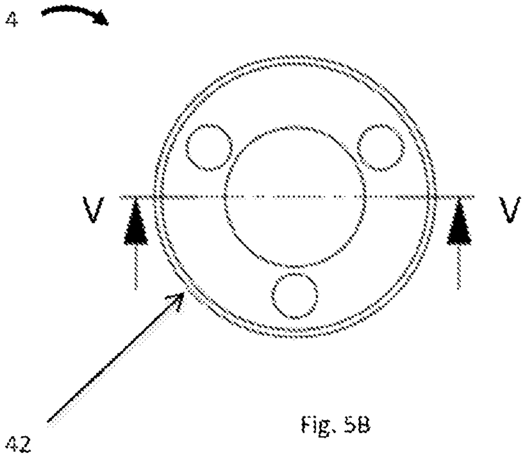
Figure 5C:
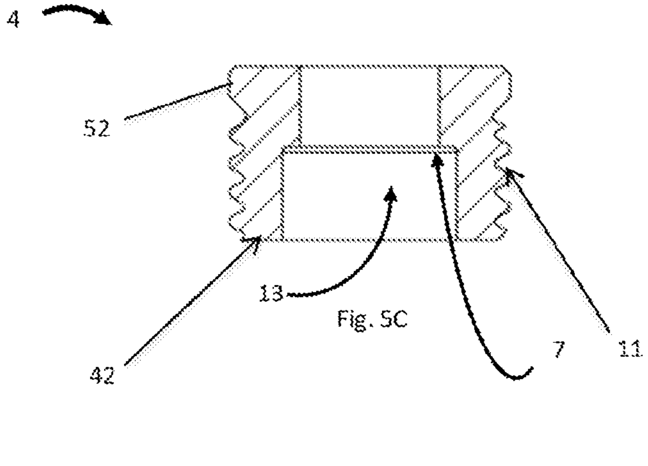

As already mentioned, the added ring 4 comprises a first member 41 (shown on FIGS. 4A to 4C). This first member is mainly used to make the assembly to the glenosphere 2. In the embodiment described, this assembly is made by clipping the first member 41 in the housing 9 of the glenosphere 2. To do this, the first member is provided with teeth present at the ends of elastically deformable peripheral means (consisting of fins 21), forming together the rib 14. These fins 21 are split (as shown in particular on FIGS. 3A, 4A and 4C) to confer to the first member 41 the elastic properties necessary to clip it in the groove 16.

The ring further comprises a second member 42 positioned and shaped so as to constrain the first member 41 in its clipped position, in particular when tightening the tightening screw 5. This second member 42 corresponds to a spacer between the first member and the tightening screw 5 and therefore acts as a lock for the first member 41. This second member 42 (FIGS. 5A to 5C), of cylindrical shape, has a diameter less than that of the first member 41, so that it can be assembled in the first member 41. In the embodiment described, this assembly is formed by screwing. To do this, the second member 42 comprises a radial and external threaded portion 11 of shape complementary to the internal radial tapped portion 10 of the first member 41. Advantageously, the second member 42 is screwed to the first member 41 in the direction opposite to that when tightening the tightening screw 5. In other words, the second member 42 is screwed to the first member 41 in the direction opposite to that when tightening the glenosphere into the patient's bone or into the metaglene 3. Thus, this reduces the risks of the first member 41 becoming unscrewed from the second member 42 during the step of tightening the tightening screw 5. Advantageously, the tapped portion 10 and the threaded portion 11 have a left hand pitch or a right hand pitch. In addition, the threaded portion 11 is preferably a metric thread, a buttress thread or a square thread. Lastly, the pitch of the tapped portion 10 and the threaded portion 11 can be standardized and/or fine. Consequently, the pitch is advantageously between 0.5 mm and 2 mm, which produces a very fine pitch.

The second member 42 comprises a collar 52 at its distal end which, when the second member 42 is in the final position inside the first member 41 (in other words when it has been screwed in completely), engages in the circular channel 51 provided in the first member 41. Thus, this final position between the first member 41 and the second member 42 is locked so that they cannot separate from each other. In a variant not shown, these locking means (in other words the collar and the channel) could respectively be provided on the first member and on the second member. According to another variant not shown of the invention, the locking means can, as an alternative or in addition, comprise at least one clip and at least one hole configured to be crossed by the clip so that the assembly can also be locked in the final position between the first member and the second member of the added ring. This clip and this hole can respectively be provided on the first member and on the second member and vice versa. In order to lock with a greater locking force, the locking means may comprise several clips and several dedicated through-holes and/or several collars and several dedicated channels.

In addition, this second member 42 comprises an internal spotface which forms said bearing surface 7 (FIGS. 3A to 3C) for the screw head 6 and has a through-hole which defines the central hole 13 crossed by the tightening screw 5. The second member 42 therefore comprises a bearing surface 7 forming a stop for the head 6 of the screw 5 when it is tightened.

The added ring 4 comprises a large contact area between the first member 41 and the second member 42, in other words the entire contact area between the thread 11 of the second member and the tapping 10 of the first member 41. Thus, when tightening the tightening screw 5, stresses are applied to the second member 42 which, due to its configuration that is more rigid than that of the first member 41, absorbs a large portion and only transmits a smaller portion of these stresses. This smaller portion is homogeneously distributed over the first member 41 via the contact area between the tapping 10 and the thread 11, then the resulting portion is itself transmitted to the inner side of the housing 9 of the ceramic glenosphere 2, mainly via the radial contact between the rib 14 and the groove 16, but also via the direct contact between the deformable fins 21 and the inner side of the housing 9 of the glenosphere 2. Consequently, stresses caused by tightening the glenosphere 2 on the metaglene 3 are transmitted to a lesser extent and distributed more homogeneously, which finally reduces the force of the stresses undergone locally by the ceramic glenosphere 2, reducing the risk of cracking or breaking the glenosphere.

As already mentioned, the invention is not limited to the embodiments described. As mentioned previously, the invention can be applied to any type of joint implant having a ceramic joint surface and being screwed and tightened using at least one tightening screw, on the patient's bone or on an intermediate element attached to said bone. For example, the invention also relates to implants for hip or knee prostheses.

LIST OF REFERENCES

1: implant
2: main body/glenosphere
3: metaglene
4: added ring
5: tightening screw
6: head of the tightening screw
7: bearing surface
8: joint outer surface
9: housing of the main body
10: tapped portion/tapping
11: threaded portion/thread
12: chamber
13: central hole of the ring
14: rib
16: groove
21: elastically deformable fins
41: first member of the added ring
42: second member of the added ring
51: channel
52: collar

What is claimed is:

1. A prosthesis joint implant (1) comprising:

a main body made of ceramic and comprising a joint outer surface made of ceramic, of concave or convex shape, at least one tightening screw configured to attach to a patient's bone, the main body or configured to attach to said patient's bone an intermediate element, at least one added ring in the main body and forming with it a chamber trapping the head of the tightening screw and comprising a bearing surface forming a stop for said head of the tightening screw, the added ring being configured to be in contact with the tightening screw during said tightening, the added ring comprising a central hole crossed by the tightening screw, the added ring being configured to homogeneously distribute in the main body the mechanical stresses caused by tightening the tightening screw, the added ring comprising a first member forming the outer surface of the added ring and comprising a clipping device for clipping to the main body and a second member acting as a spacer between the first member and the tightening screw, said second member being assembled in the first member, forming said bearing surface and defining the central hole, the first member and the second member being two members separate from each other and comprising a locking device configured to prevent them from separating from each other after assembly.

2. The prosthesis joint implant according to claim 1, wherein the first member comprises a tapped portion and the second member comprises a corresponding threaded portion, the threaded portion and the tapped portion being configured so that the second member can be screwed to the first member, preferably, the second member being screwed to the first member in the direction opposite to that when tightening the tightening screw.

3. The prosthesis joint implant according to claim 2, wherein the tapped portion and the threaded portion have a left-hand pitch or a right-hand pitch, preferably of between 0.5 mm and 2 mm, the threaded portion preferably being a metric thread, a buttress thread or a square thread.

4. The prosthesis joint implant according to claim 1, wherein the locking device comprise a circular channel and a collar configured to engage in said channel the channel being formed on the first member or on the second member and the collar being respectively formed on the second member or the first member.

5. The prosthesis joint implant according to claim 1, wherein the locking device comprises at least one clip and at least one hole configured to be crossed by the clip, the clip being formed on the first member or on the second member and the hole being respectively formed on the second member or the first member.

6. The prosthesis joint implant according to claim 1, wherein the first member comprises an elastically deformable peripheral device.

7. The prosthesis joint implant according to claim 1, wherein the main body is a glenosphere, the tightening screw being configured to tighten the glenosphere onto a metaglene adapted to be attach attached to the patient's glenoid.

8. The prosthesis joint implant according to claim 7, wherein the diameter of the glenosphere is between 30 and 46 mm.

9. The prosthesis joint implant according to claim 1, wherein the main body is a ceramic tibial plateau, a knee condyle, an anatomic glenoid, a hip acetabulum or a ceramic cup.

10. A joint prosthesis comprising an implant according to claim 1.

* * * * *